US011344725B2

(12) United States Patent
Várkuti

(10) Patent No.: US 11,344,725 B2
(45) Date of Patent: May 31, 2022

(54) NEURONAL COMMUNICATION SYSTEM

(71) Applicant: CereGate GmbH, Hamburg (DE)

(72) Inventor: Bálint Várkuti, Munich (DE)

(73) Assignee: CereGate GmbH, Hamburg (DE)

(*) Notice: Subject to any disclaimer, the term of this patent is extended or adjusted under 35 U.S.C. 154(b) by 2 days.

(21) Appl. No.: 16/380,036

(22) Filed: Apr. 10, 2019

(65) Prior Publication Data
US 2020/0269049 A1  Aug. 27, 2020

(30) Foreign Application Priority Data
Feb. 27, 2019 (DE) .................... 10 2019 202 666.4

(51) Int. Cl.
*A61N 1/36* (2006.01)
*A61N 1/05* (2006.01)
(Continued)

(52) U.S. Cl.
CPC .......... *A61N 1/36057* (2013.01); *A61B 5/055* (2013.01); *A61B 5/377* (2021.01);
(Continued)

(58) Field of Classification Search
CPC ............. A61N 1/36057; A61N 1/0531; A61N 1/3606; A61N 5/0601; A61N 5/0622; A61B 5/0484; A61B 5/055; A61B 6/032
See application file for complete search history.

(56) References Cited

U.S. PATENT DOCUMENTS

| 4,441,202 A * | 4/1984 | Tong .................. G10L 25/93 381/326 |
| 4,445,512 A | 5/1984 | Krupka et al. |

(Continued)

FOREIGN PATENT DOCUMENTS

| DE | 102019202666 A1 | 8/2020 |
| DE | 102019209096 A1 | 12/2020 |

(Continued)

OTHER PUBLICATIONS

First Office Action dated Oct. 16, 2019 for German Application No. DE 10 2019 202 666.4, 14 pp.
(Continued)

*Primary Examiner* — Michael W Kahelin
(74) *Attorney, Agent, or Firm* — Kowert, Hood, Munyon, Rankin & Goetzel, P.C.

(57) ABSTRACT

The present invention relates to a system for providing neuronal stimulation signals configured to elicit sensory percepts in the cortex of an individual, comprising means for obtaining spatial information relating to the actual or planned position of at least one neuronal stimulation means relative to at least one afferent axon targeting at least one sensory neuron in the cortex of the individual and means for determining at least one neuronal stimulation signal to be applied to at least one afferent axon via the at least one neuronal stimulation means based at least in part on the obtained spatial information.

Figure 1:
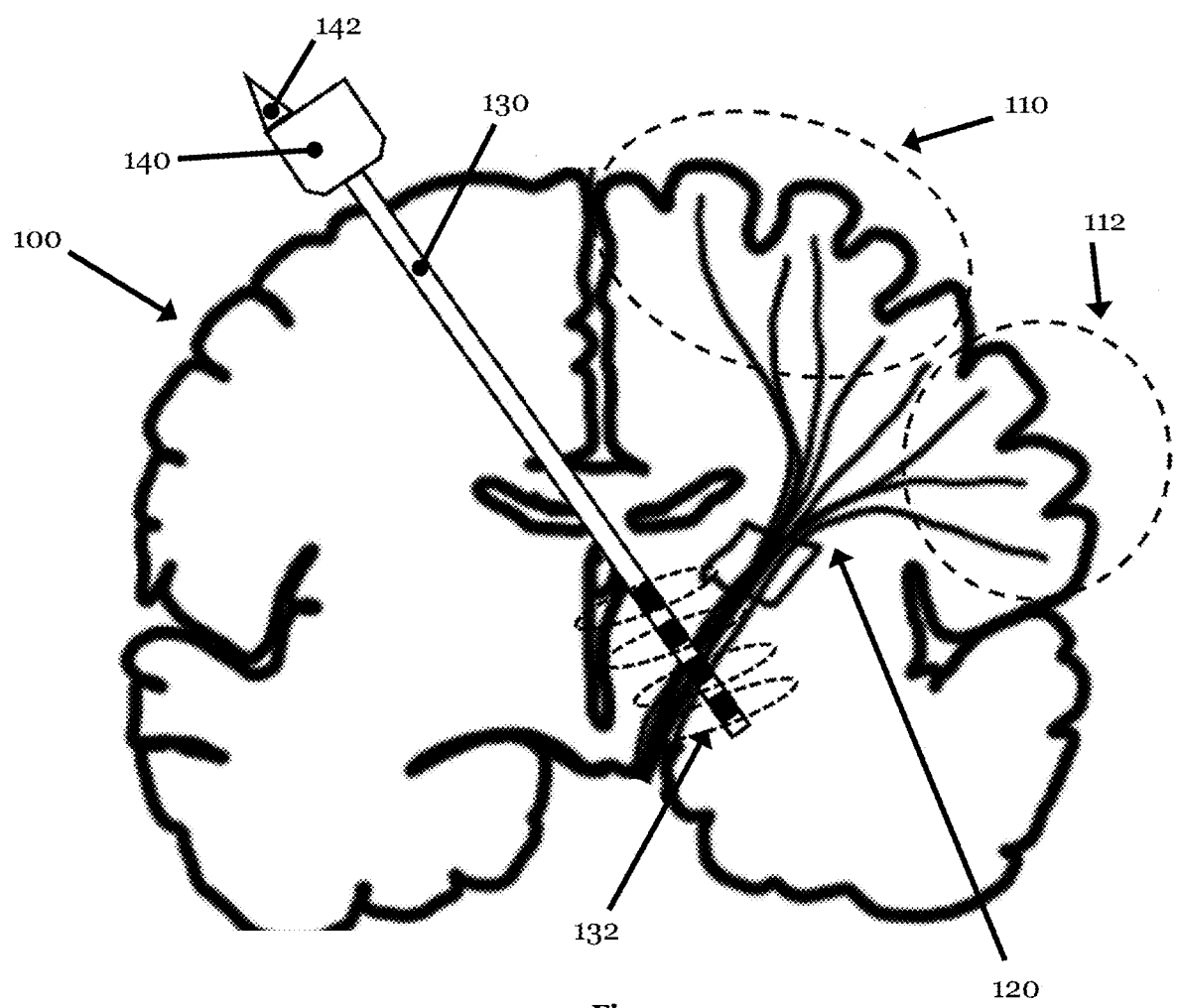

The present invention further relates to a system for communicating conceptual information to an individual, comprising means for selecting at least one neuronal stimulation signal to be applied to at least one afferent axon targeting at least one sensory neuron in the cortex of the individual, wherein the at least one neuronal stimulation signal corresponds to the conceptual information to be communicated and means for transmitting the at least one neuronal stimulation signa to at least one neuronal stimulation means of the individual.

20 Claims, 9 Drawing Sheets

(51) Int. Cl.
  *A61N 5/06* (2006.01)
  *A61B 6/03* (2006.01)
  *A61B 5/055* (2006.01)
  *A61B 5/377* (2021.01)

(52) U.S. Cl.
  CPC ............ *A61B 6/032* (2013.01); *A61N 1/0531* (2013.01); *A61N 1/3606* (2013.01); *A61N 5/0601* (2013.01); *A61N 5/0622* (2013.01)

(56) References Cited

U.S. PATENT DOCUMENTS

| | | | |
|---|---|---|---|
| 4,488,555 A | 12/1984 | Imran | |
| 5,800,535 A * | 9/1998 | Howard, III | A61N 1/0531 623/10 |
| 6,400,989 B1 * | 6/2002 | Eckmiller | A61N 1/36038 607/54 |
| 7,751,884 B2 | 7/2010 | Ternes et al. | |
| 7,774,056 B2 | 8/2010 | Torgerson | |
| 8,193,766 B2 | 6/2012 | Rondoni et al. | |
| 8,290,596 B2 | 10/2012 | Wei et al. | |
| 8,352,029 B2 | 1/2013 | Ternes et al. | |
| 8,364,271 B2 | 1/2013 | De Ridder | |
| 8,380,314 B2 * | 2/2013 | Panken | A61N 1/3605 607/45 |
| 8,423,145 B2 | 4/2013 | Pless et al. | |
| 8,437,858 B2 * | 5/2013 | Dapper | A61N 1/025 607/53 |
| 8,475,172 B2 | 7/2013 | Lieberman et al. | |
| 8,494,633 B2 | 7/2013 | Tobacman | |
| 8,509,904 B2 | 8/2013 | Rickert et al. | |
| 8,812,128 B2 | 8/2014 | Kothandaraman | |
| 9,095,314 B2 | 8/2015 | Osorio et al. | |
| 9,357,938 B2 | 6/2016 | Ang et al. | |
| 9,526,896 B2 * | 12/2016 | Greenberg | A61N 1/36185 |
| 9,636,497 B2 | 5/2017 | Bradley et al. | |
| 9,713,720 B2 | 7/2017 | Zhu | |
| 9,974,478 B1 | 5/2018 | Brokaw et al. | |
| 10,568,559 B2 | 2/2020 | Parker et al. | |
| 2003/0065366 A1 | 4/2003 | Merritt et al. | |
| 2006/0129205 A1 | 6/2006 | Boveja et al. | |
| 2006/0241717 A1 | 10/2006 | Whitehurst et al. | |
| 2006/0241718 A1 | 10/2006 | Tyler et al. | |
| 2007/0027397 A1 | 2/2007 | Fischell et al. | |
| 2007/0250134 A1 | 10/2007 | Miesel et al. | |
| 2008/0129517 A1 | 6/2008 | Crosby et al. | |
| 2008/0139954 A1 | 6/2008 | Day et al. | |
| 2009/0264789 A1 | 10/2009 | Molnar et al. | |
| 2009/0306741 A1 | 12/2009 | Hogle et al. | |
| 2010/0057161 A1 | 3/2010 | Machado et al. | |
| 2010/0094382 A1 | 4/2010 | Pezaris et al. | |
| 2010/0249879 A1 * | 9/2010 | Bracker | A61N 1/36039 607/56 |
| 2013/0150914 A1 | 6/2013 | Kelly et al. | |
| 2013/0253299 A1 | 9/2013 | Weber et al. | |
| 2014/0081348 A1 | 3/2014 | Fischell | |
| 2014/0379046 A1 | 12/2014 | Tcheng et al. | |
| 2015/0018724 A1 | 1/2015 | Hsu et al. | |
| 2015/0073492 A1 | 3/2015 | Kilgard et al. | |
| 2015/0290453 A1 | 10/2015 | Tyler et al. | |
| 2016/0022992 A1 * | 1/2016 | Franke | A61N 1/36046 607/59 |
| 2016/0121118 A1 * | 5/2016 | Franke | A61N 1/36046 607/53 |
| 2017/0182328 A1 | 6/2017 | Moffitt | |
| 2018/0050198 A1 | 2/2018 | Mazanec et al. | |
| 2019/0030338 A1 | 1/2019 | Wu et al. | |
| 2020/0269049 A1 | 8/2020 | Varkuti | |

FOREIGN PATENT DOCUMENTS

| | | |
|---|---|---|
| EP | 2552304 B1 | 9/2015 |
| EP | 3229893 A1 | 10/2017 |
| EP | 3431138 A1 | 1/2019 |
| EP | 2486897 B1 | 5/2019 |
| KR | 20170132055 | 12/2017 |
| KR | 101841625 B1 | 5/2018 |
| WO | 2012003451 A2 | 1/2012 |
| WO | 2012003451 A3 | 1/2012 |
| WO | 2016116397 A1 | 7/2016 |
| WO | 2018057667 A1 | 3/2018 |
| WO | 2018109715 A1 | 6/2018 |
| WO | 2020174051 A1 | 9/2020 |

OTHER PUBLICATIONS

Designing a Thalamic Somatosensory Neural Prosthesis: Consistency and Persistence of Percepts Ecoked by Electrical Simulation, IEEE Transactions on neural Systems and Rehabilitatinonengineering; IEEE Service Center, New York, vol. 19, No. 5, 6 pgs.
Invitation to Pay Additional Fees and, Where Applicable, Protest Fee and Partial International Search Report for PCT/EP2020/055156, dated May 29, 2020, 21 pgs.
Beauchamp et al., "Dynamic Electrical Stimulation of Sites in Visual Cortex Produces Form Vision in Sighted and Blind Humans," bioRxiv preprint, http://dx.doi.org/10.1101/462697, Nov. 5, 2018.
Lee et al., "Engineering Artificial Somatosensation Through Cortical Stimulation in Humans," Frontiers in Systems Neuroscience, www.frontiersin.org, Jun. 4, 2018, vol. 12, Article 24.
Roelfsema et al., "Mind Reading and Writing: The Future of Neurotechnology," Trends in Cognitive Sciences, https://doi.org/10.1016/j.tics.2018.04.001, May 6, 2018, Elsevier Ltd.
Anderson et al., "Optimized Programming Algorithm for Cylindrical and Directional Deep Brain Stimulation Electrodes," https://doi.org/10.1088/1741-2552/aaa14b, Journal of Neural Engineering, Jan. 24, 2018, IOP Publishing Ltd.
Swan et al., "Sensory Percepts Induced by Microwire Array and DBS Microstimulation in Human Sensory Thalamus," https://doi.org/10.1016/j.brs.2017.10.017, Brain Stimulation 11 (2018) 416-422, Elsevier Inc.
Donati, A., Shokur, S., Morya, E. et al. "Long-Term Training with a Brain-Machine Interface-Based Gait Protocol Induces Partial Neurological Recovery in Paraplegic Patients" Sci Rep 6, 30383 (2016); https://doi.org/10.1038/srep30383, 16 pgs.
Examination Report for German Application No. 1020192014752.6, dated Jun. 16, 2020, 8 pgs.
Yadav, A.P., Li, D. & Nicolelis, M.A.L. : "A Brain to Spine Interface for Transferring Artificial Sensory Information". Sci Rep 10, 900 (2020), 15 pgs.
"Sensory Electrical Stimulation Cueing May Reduce Freezing of Gait Episodes in Parkinson's Disease"; L. Rosenthal et. al.; Hindawi Journal of Healthcare Engineering; 2018, Article ID 4684925, 6 pgs.
"Effect of rhythmic auditory cueing on parkinsonian gait: A systematic review and meta-analysis"; S. Ghai et al.; Nature Scientic Reports; (2018) 8:506; DOI:10.1038/s41598-017-16232-5, 19 pgs.
Examination Report for German Application No. 1020192014752.6, dated Apr. 16, 2021, 5 pgs.
First Office Action dated Mar. 17, 2020 for German Application No. DE102019209096.6, 13 pages.
Heming E., et al., "Designing a Somatosensory Neural Prosthesis: Percepts Evoked by Different Patterns of Thalamic Stimulation," Journal of Neural Engineering, Dec. 1, 2010, vol. 7 (6), 7 pages.
International Preliminary Report issued in International Application No. PCT/EP2020/055156, dated Sep. 10, 2021, 17 pages.
International Search report and Written Opinion issued in International Application No. PCT/EP2020/055156, dated Jul. 21, 2020, 22 pages.
Office Action for European Application No. 20200707624, dated Dec. 7, 2021, 14 pages.

* cited by examiner

NEURONAL COMMUNICATION SYSTEM

1. PRIORITY INFORMATION

This application claims priority to German Patent Application number DE to 2019 202 666.4, titled "Neuronal Communication System" and filed on Feb. 27, 2019, which is hereby incorporated by reference in its entirety, as though fully and completely set forth herein.

2. TECHNICAL FIELD

The present invention relates to signal and data processing systems for providing neuronal stimulation signals that may be used for direct neuronal communication with an individual.

3. TECHNICAL BACKGROUND

Communication with a human individual conventionally relies on providing sensory stimuli to the sensory organs of the individual, for instance, as a sequence of images, visual symbols, sounds and/or somatosensory stimuli. Examples for such information carrying sequence of sensory stimuli are: spoken language, script, Morse code, Braille, sign language, etc., wherein, for instance, the information content of spoken language and Morse code is communicated to the individual via auditory stimuli, the information content of Braille via somatosensory stimuli and the information content of script and sign language via visual stimuli.

To extract the communicated information, the sensory organs (e.g. the inner hair cells of the cochlea or the rod cells of the retina) transform the input energy of a respective sensory stimulus into neuronal excitation signals (i.e. into a sequence of action potentials). These neuronal excitation signals are then transmitted via afferent sensory nerve fibers to the brain and are ultimately processed by the cortex. The resulting mental re-creation of a given sensory stimulus in the cerebral cortex (i.e. the elicited cortical excitation pattern) is called the sensory percept associated with a given sensory stimulus. Sensory percepts can either be conscious or unconscious. For instance, a human trained in reading Braille with his fingertips does no longer consciously perceive the exact dot pattern of every Braille symbol of a Braille text but directly obtains a conscious understanding of the information content communicated via the sequence of Braille symbols forming the text.

Importantly, in many cases, the communicated information goes beyond the mere sensory percept. As an example, consider Morse code. Each Morse code message elicits a certain sequence of sensory precepts in the auditory cortex, i.e. a sequence of perceived tones having a certain duration (e.g. long or short) and having a certain pitch, (e.g. 500 Hz).

However, the cortex of an individual can also extract complex conceptual information from such sequence of sensory percepts of the cortex, for instance, extracting a request to provide help for the crew of a drowning ship encoded in a specific sequence of nine consecutive tones in Morse code. In the remainder of this application the term "conceptual information" is thus to be understand broadly, in the sense to comprise any information content that can be extracted by the cortex and goes beyond eliciting a mere sensory percept. Moreover, in many cases, the cortex acquires the capability to extract complex conceptual information from a given sequence of sensory percepts via learning. For instance, a radio operator first must learn the semantics of Morse code to understand an SOS signal.

Certain diseases and/or injuries of the sensory organs (e.g. deafness, blindness, etc.) may impair the communication capability of an individual. For some of these conditions, sensory stimulation devices such as cochlea or retina implants are well known in the prior art. Moreover, recent advances in data and signal processing as well as sensory stimulation technology have resulted in devices for eliciting visual percepts via stimulating somatosensory cells in the human tongue (see for example US 2006/0241718 A1 and US 2015/0290453 A1). In principle, such devices can also be used for communication, e.g. for reading script or understanding general visual symbols.

In addition, considerable scientific research is directed to the development of so-called computer brain interfaces (CBIs) that allow to directly elicit certain sensory percepts in the cortex of an individual without stimulation of the sensory organs and/or the peripheral nervous system. For instance, the recent publication "*Dynamic Electrical Stimulation of Sites in Visual Cortex Produces Form Vision in Sighted and Blind Humans*"; M. S. Beauchamp et. al.; DOI. 10.1101/462697, describes how a subdural electrode array can be used to directly elicit visual percepts in the visual cortex of an individual allowing for immediate recognition of a variety of letter shapes without training and high accuracy. Similar methods and stimulation paradigms are described in "*Engineering Artificial Somatosensation Through Cortical Stimulation in Humans*"; B. Lee et. al.; *Frontiers in Systems Neuroscience*, 12; 2018; relating to eliciting somatosensory percepts via cortical stimulation with a subdural mini-electrocorticography grid. A general overview on trends in neuronal stimulation and measurement technology is provided by the article "*Mind Reading and Writing: The Future of Neurotechnology*"; P. R. Roelfsema et al.; *Trends in Cognitive Sciences;* 5; 2018.

A related research direction is discussed in "*Sensory percepts induced by microwire array and DBS microstimulation in human sensory thalamus*"; B. D. Swan et. al.; *Brain Stimulation;* 11; 2018. Specifically, the authors could show that it is possible to use deep brain stimulation (DBS) electrodes to evoke somatosensory percepts of the hand or arm by electrostimulation of the sensory thalamus in humans.

Further, the publication "*Optimized programming algorithm for cylindrical and directional deep brain stimulation electrodes*"; D. N. Anderson et. al.; *Journal of Neural Engineering;* 15; 2018; relates to using magnetic resonance imaging (MRI) and diffusion tensor imaging (DTI) to build a finite element method (FEM) model of a DBS electrode used for treatment of movement and psychiatric disorders (e.g. morbus Parkinson) and of the brain tissue surrounding the DBS electrode. The resulting FEM model can then be used to find optimized stimulation parameters for stimulating efferent cortico-motor axons via the DBS electrode.

Further, WO 2016/116397 A1 relates to a medical data processing method for determining an orientation of nerve fibers relative to a non-physiological electric field, produced by a stimulation electrode based on medical image data of nerve tissue comprising white matter nerve fibers. Additional prior art that may be relevant is provide by KR 10 184 1625 and EP 3 431 138.

However, the neuronal stimulation paradigms and systems known from the prior art have various deficiencies. First, CBIs that employ direct cortical stimulation, e.g. via a subdural micro-electrode array, can only stimulate the outer layers of the cortex and therefore neglect or at least do not fully respect the hierarchical organization of cortical processing. This results in many cases in non-physiological stimulation and/or excitations patterns potentially degrading the quality of the elicited sensory percepts. In other words, the neurons in the outer layer of the cortex are adapted to receive neuronal signals that have been pre-processed by various lower cortical layers and/or deeper brain regions and thus are in general not adapted to directly receive and process electric stimulation signals provided by a subdural electrode array.

Moreover, the spatial resolution of current micro-electrode arrays is still far too coarse as to be able to elicit physiological correct sensory percepts. In addition, it is well known in the art that the neuron and blood vessel rich environment of the cortex can easily lead to scar tissue formation and/or gliosis resulting in a reduced performance of the micro-electrode array over time.

Furthermore, micro-fabricated implants with single-unit/single-neuron interface capabilities or electro-cortical grids are usually anchored between the brain and the skull. Since the brain moves with every pulsation of the heart inside the cranial cavity, or during expose to acceleration forces e.g. during physical activity, the relative position of the surface implants can move over time—leading to a further degradation of the CBI.

Concerning the stimulation of sensory percepts via DBS of the thalamus, the methods and systems described in the prior art completely lack sufficient spatial and/or sensory resolution and thus can by no means be used for robust and reproducible stimulation of desired sensory percepts. Furthermore, they only aim at reproducing the natural sense of sensation in the human somatosensory system e.g. for application as a neural prosthetic for amputees.

It is thus the problem of the present invention to provide novel neuronal stimulation systems that improve the known systems such that the above outlined disadvantages of the prior art are at least partially overcome.

4. SUMMARY OF THE INVENTION

The above-mentioned problem is at least partly solved by the subject matter of the independent claims of the present application. Exemplary embodiments of the invention are the subject of the depended claims.

In one embodiment, the present invention provides a system for providing neuronal stimulation signals configured to elicit a sensory percept in the cortex of an individual, comprising: means for obtaining spatial information relating to the actual or planned position of at least one neuronal stimulation means relative to at least one afferent axon targeting at least one sensory neuron in the cortex of the individual and means for determining at least one neuronal stimulation signal to be applied to at least one afferent axon via the at least one neuronal stimulation means based at least in part on the obtained spatial information.

For instance, such systems are capable of determining specific neuronal stimulation signals that are tailored to stimulate a desired sub-population of sensory neurons in the cortex. For example, some neuronal stimulation signals may be engineered such that they are configured to elicit somatosensory percepts of the left hand of the individual, while other stimulation signal are configured to elicit a touch sensation of the tongue. By using the obtained spatial information of the electrode position relative to afferent axons targeting the sensory cortex the system can establish a correspondence between the actual form of the neuronal stimulation signal and a target region and/or a target percept in the sensory cortex. For instance, such neuronal stimulation signal may comprise a sequence of current pulses characterized by a pulse width, a pulse frequency, a pulse amplitude and/or a pulse shape.

In this manner, the provided system facilitates directly eliciting certain sensory percepts in the cortex of an individual without stimulation of the sensory organs and/or the peripheral nervous system.

Further, such neuronal stimulation signals may be configured to elicit a sequence of action potentials in the at least one afferent axon targeting the sensory neurons in the cortex of the individual. Moreover, the at least one axon may be a thalamocortical axon, i.e. an axon that transmits sensory information from the thalamus to the sensory cortex of an individual.

By providing neuronal stimulation signals that are configured to elicit action potentials in axons targeting the sensory cortex, it can be ensured that the stimulation for a given sensory percept enters the cortex via the physiological correct signaling pathway, e.g. via action potentials of a thalamocortical axon. In this manner, correct cortical processing of the neuronal stimulation signals can be ensured and the quality of the elicited sensory percept can be enhanced.

Further, the means for obtaining the spatial information may comprise means for obtaining tractography information and/or neuronal connectivity information for the at least one afferent axon, preferably comprising magnetic resonance imaging data, diffusion tensor imaging data and/or anatomic reference data.

By using such tractography information and/or neuronal connectivity information (e.g. information on synaptic connections between axons and sensory neurons) for the axons that target the sensory cortex of the individual the actual form of the neuronal stimulation signals can be even further be tailored to elicit a desired sensory percept in a desired region of the sensory cortex. In particular, DTI data may allow to also take in to account individual neuroanatomical variations and/or neuronal plasticity for determining the desired neuronal stimulation signals for a given target percept and/or target region of the sensory cortex.

Further, the means for obtaining the spatial information may comprise means for obtaining neuroimaging data of a volume of brain tissue surrounding at least a portion of the actual or planned position of the at least one neuronal stimulation means, preferably comprising computer tomography data and/or magnetic resonance imaging data.

In this way, the system can also take into account the physical and in particular electrical properties of the brain tissue surrounding the neural stimulation means. For instance, the neuroimaging data may be used to determine the electric conductivity of the surrounding brain tissue. In this way, the specificity and accuracy of the determined neuronal stimulation signal for certain afferent axons and/or sensory neurons can further be enhanced.

Further, the means for determining the neuronal stimulation signal may comprise means for determining an excitation probability of the at least one afferent axon and/or the at least one sensory neuron based at least in part on the obtained spatial information, preferably by using a finite element method and/or a neuronal compartment model.

In this manner active electric properties (e.g. the non-linear neuronal excitability) of the at least one axon can be taken into account by the system when determining the at least one neuronal stimulation signal, thereby further enhancing the specificity and accuracy of the neuronal stimulation signal for a desired target axon and/or target stimulation region in the sensory cortex.

The means for determining the at least one neuronal stimulation signal may be further configured to determine the at least one neuronal stimulation signal based at least in part on at least one of: at least one desired type of percept to be elicited by the at least one neuronal stimulation signal; at least one desired target area of the cortex comprising the at least at least one targeted sensory neuron; an optimization procedure maximizing the number of different sensory percepts that can be perceived by the individual when the determined at least one neuronal stimulation signal is applied to the at least one afferent axon via the at least one neuronal stimulation means.

In this manner, the amount of information that can be communicated via eliciting sensory percepts by a given stimulation means can be enhanced. Furthermore, by interfacing with axonal structures at points deep within the brain via dynamically configured electrical pulses information can be transmitted to the full range of superficial cortical processing zones these axons project to—without having to cover the entire surface area with invasive macro- or microstimulation implants.

In another embodiment the present invention provides a system for stimulating sensory neurons in a cortex of an individual, comprising: means for storing relations between sensory percepts of the individual and corresponding neuronal stimulation signals to be applied to at least one afferent axon targeting the sensory neurons of the individual and means for selecting and transmitting at least one of the neuronal stimulation signals to at least one neuronal stimulation means of the individual.

This embodiment greatly improves the efficiency and flexibility of eliciting desired sensory percepts in the cortex of an individual. For instance, a communication device that interfaces with the provided system can easily determine and directly transmit the specific neuronal stimulation signal corresponding to a desired sensory percept to be elicited in the cortex of an individual via stimulation of afferent axons targeting sensory neurons in the cortex of the individual.

For instance, in some embodiment of the present invention, the stored relations between the sensory percepts and the corresponding neuronal stimulation signals are based at least in part on one or more of: spatial information for the at least one afferent axon, spatial information for the at least one neuronal stimulation means, neuronal connectivity information for the at least one afferent axon, an electric field distribution associated with the at least one neuronal stimulation means, functional neuroimaging data for the individual, diffusion tensor imaging data for the individual, neuroanatomical reference data being relevant for the individual, cortical excitation data for the individual, perceptual and/or conceptual learning data for the individual, sensory perception data for the individual, behavioral data based at least in part on subjective experiences of the individual, an optimization procedure for maximizing the number of sensory percepts that can be perceived, preferably simultaneously, by the individual when the corresponding neuronal stimulation signal is transmitted to the at least one neuronal stimulation means of the individual.

In some embodiments, the provided system may further comprise at least one neuronal stimulation means adapted to induce a sequence of action potentials in the at least one afferent axon corresponding to the at least one neuronal stimulation signal.

Via integrating the neural stimulation means into the provided system the overall system efficiency can be enhanced and system complexity be reduced, e.g. by using customized wired or wireless interfaces for the at least one neuronal stimulation means.

To further improve the versatility and the degree of system integration, in some embodiments, the means for transmitting the at least one neuronal stimulation signal may comprise at least one of: a digital signal processor; a digital to analog converter; a radio frequency transmitter; a radio frequency receiver; an analog and/or digital signal amplifier; radio frequency mixing circuitry; low-pass, high-pass and/or band-pass circuitry; wireless communication circuitry; and impedance matching circuitry.

In some embodiments, the perceptual and/or conceptual learning data on which the relations between sensory percept and corresponding neuronal stimulation signal may be generated based at least in part on one or more of: the individual participating in a perceptional and/or conceptual learning procedure and the individual being analyzed by a functional neuroimaging device, preferably functional magnetic resonance imaging while receiving the at least one neuronal stimulation signal.

In this manner, the ability of the human brain to learn how to distinguish even fine variations in sensory percepts can be used to improve the system performance. The finer the resolution of the unique perceptual patterns the more concepts or messages can be uniquely associated with the neural stimulation patterns, similar to the relationship between a sign and its meaning. The more signs can be perceived the more meaning can be communicated.

In a further embodiment, the present invention provides a system for communicating conceptual information to an individual, comprising: means for selecting at least one neuronal stimulation signal to be applied to at least one afferent axon targeting at least one sensory neuron in the cortex of the individual, wherein the least one neuronal stimulation signal corresponds to the conceptual information to be communicated and means for transmitting the at least one neuronal stimulation signal to at least one neuronal stimulation means of the individual.

For instance, the conceptual information may comprise at least one of: a letter, a number, a color, a direction in space, a word, a sentence, an object, an identity of a person or animal and/or an instruction for a motor response of the individual, a position, a bio- or neurofeedback signal, a shape, an image or icon, a warning, an association, a degree of similarity, a salience signal, a rhythm, start or stop commands m or information, touch information, surface texture information, pressure information, electromagnetic field strength indication or other types of information.

Further, the means for selecting the at least one neuronal stimulation signal may comprise means for accessing a data storing means storing relations, specific for the individual, between a plurality of conceptual information and a plurality of corresponding neuronal stimulation signals.

For example, the stored specific relations may be based at least in part on conceptual learning data for the individual, the conceptual learning data associating the plurality of conceptual information with the plurality of corresponding neuronal stimulation signals.

For instance, if an individual has participated in a perceptual and/or conceptual learning procedure and has learned to identify a certain somatosensory percept (e.g. a touch sensation on the left palm) with a piece of conceptual information (e.g. a direction in space) a relation between the conceptual information and the specific neuronal stimulation signal eliciting the respective somatosensory percept can be stored in a data storing means and be accessed for subsequent communication sessions with the individual.

For instance, the at least one neuronal stimulation signal may be adapted to evoke a conscious or an unconscious sensory percept in the cortex of the individual.

Depending on the actual application and/or technology platform used for stimulation the at least on afferent axon targeting the sensory cortex of the individual, the at least one neuronal stimulation means may comprise an electric-neuronal interface means, an opto-neuronal interface means and/or a chemical-neuronal interface means.

For instance, the electric-neuronal interface means may comprise at least one stimulation electrode, preferably comprising a plurality of independently controllable electric stimulation contacts. For example, such stimulation electrode may be a multi-contact DBS electrode adapted for targeting the thalamus region of the human brain.

Given a suitable signal source such multi-contact electrodes allow for independent multi-channel current control enabling to create complex spatial electric stimulation pattern around the stimulation electrode. In this way a single electrode can be used to selectively stimulate a desired subset of axons in the vicinity of the stimulation electrode. Essentially, the number of different axons or different axon bundles that can selectively be stimulated via such multi-channel electrode correspond to different neuronal communication channels that can be established via said electrode.

To further improve the spatial resolution of the excitation pattern that can be generated, the electric-neuronal interface means may further comprises at least two independently controllable stimulation electrodes, each preferably comprising a plurality of independently controllable electric contacts.

For example, the at least one stimulation electrode may be provided by at least a part of a neuromodulation electrode implanted for a therapeutic purpose independent from the stimulation. Specifically, the portion of the neuromodulation electrode may be a portion that is not used for the therapeutic purpose.

For instance, in many cases, a DBS electrode that is used as a neuromodulator, e.g. for treatment of Parkinson, is not always active and/or may comprise independently controllable contacts that are not required for achieving the therapeutic purpose. Thus, the neuromodulation electrode can also be used for applying neuronal stimulation signals provided by a system according to the present invention.

In general, the systems provided by the present invention may provide neuronal stimulation signals for the at least one afferent axon targeting the least one sensory neuron, which may be located in at least one of: a somatosensory cortex area, an auditory cortex area, a visual cortex area, an olfactory cortex area, a gustatory cortex area, a somatosensory association cortex area, and a proprioception cortex area.

In another embodiment, the present invention provides a system for determining an implantation position or trajectory for a neuronal stimulation electrode, comprising: means for automatically identifying a plurality of afferent axons targeting sensory neurons in the cortex associated with a specific sensory modality; means for obtaining neuroanatomical imaging and/or reference data of a volume of brain tissue comprising the plurality of afferent axons and means for automatically determining the implantation position and/or implantation trajectory for the neuronal stimulation electrode based at least in part on the identified plurality of afferent axons and the obtained neuroanatomical imaging and/or reference data.

Specifically, the means for obtaining the neuroanatomical imaging data may comprise means for obtaining computer tomography and/or magnetic resonance imaging data.

For instance, the provided system allows to provide a neurosurgeon and/or a surgical robot with information on a desired implantation position and/or implantation trajectory for the neuronal stimulation electrode prior to performing the implantation of the electrode. For example, if the electrode is to be implanted for the purpose of establishing a CBI with the individual, the implantation position and/or implantation trajectory can be tailored for a specific sensory percept that is to be used for communication purposes, e.g. used to encode conceptual information to be communicated.

In some embodiments, the means for automatically determining the implantation position and/or the implantation trajectory may comprise means for optimizing a stimulation rate of at least a subset of the sensory neurons. In this way the communication bandwidth of a desired perceptual communication channel may be enhanced even prior to implantation of the electrode.

Further, the means for automatically determining the implantation position and/or the implantation trajectory may be configured to determine the implantation position and/or the implantation trajectory based at least in part on identifying at least two types of sensory percepts to be elicited by the neuronal stimulation electrode, preferably simultaneously.

In this manner the neurosurgeon and/or surgical robot is enabled to perform the implantation procedure such that at least two separate communication channels can be established for the CBI using the implanted electrode.

In essence, the present invention incorporates new methods for calibrating a neural interface optimally to the individual and explicitly builds on the brains natural ability of decoding any information-carrying signal of behavioral relevance into a subjectively-interpretable perception or translate it into the appropriate corresponding action.

5. SHORT DESCRIPTION OF THE FIGURES

Figure 2:
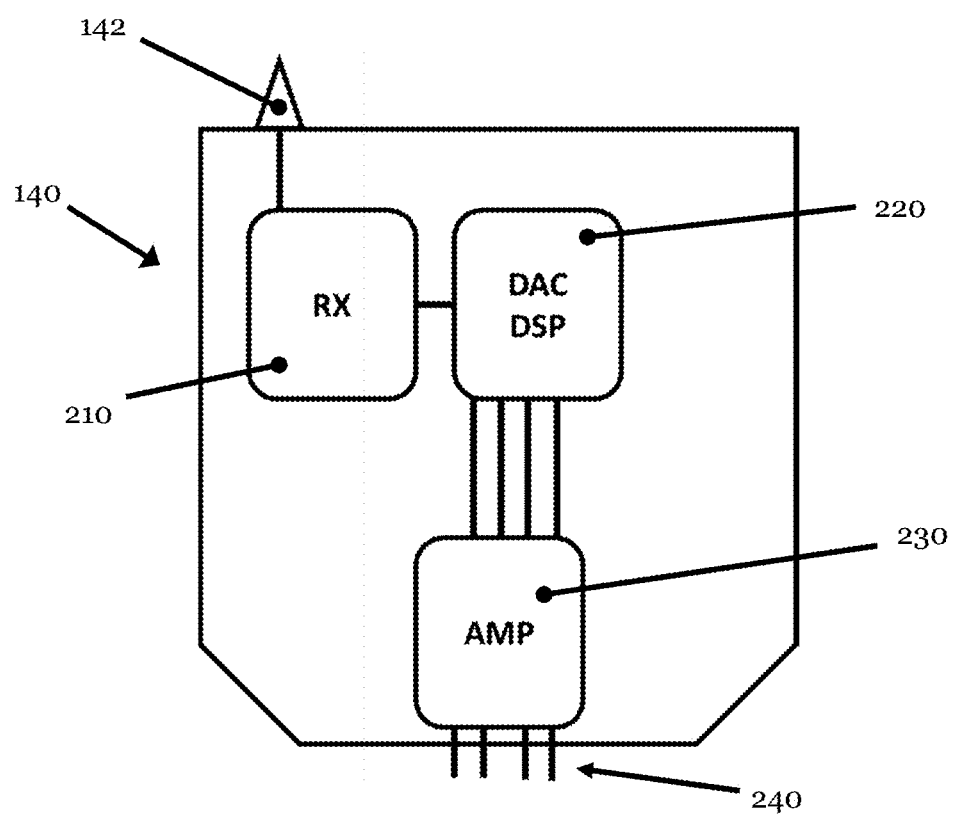
Figure 3:
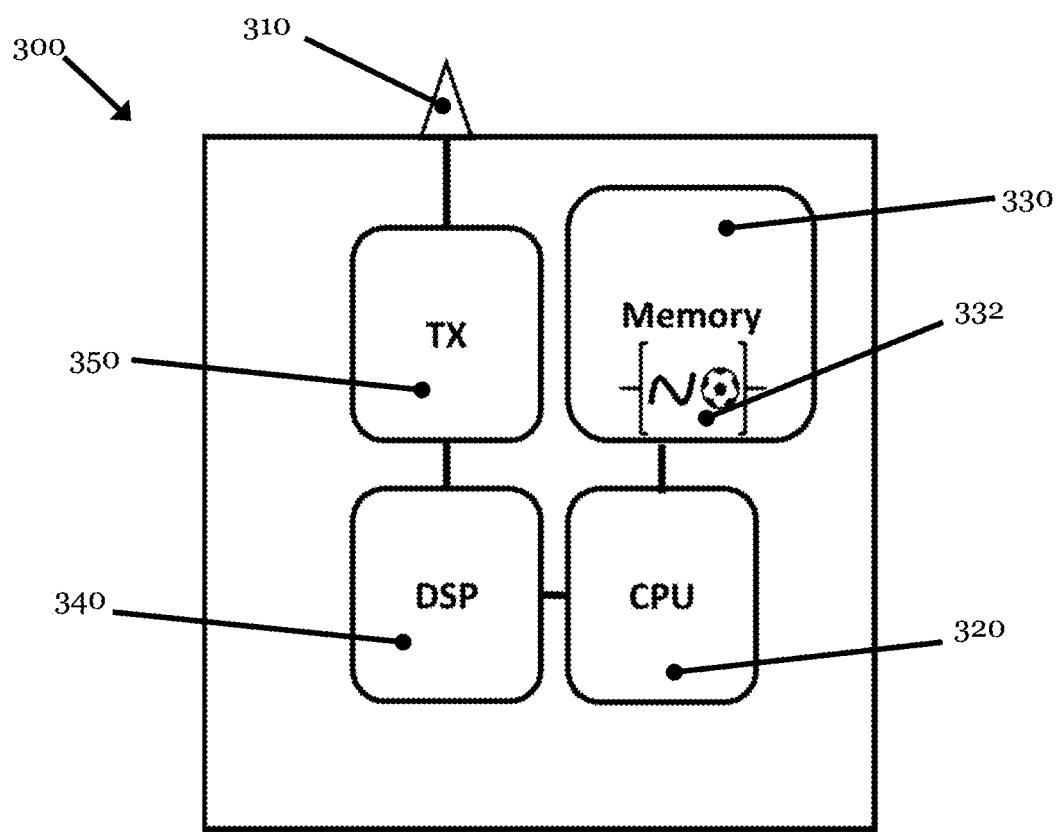
Figure 4A:
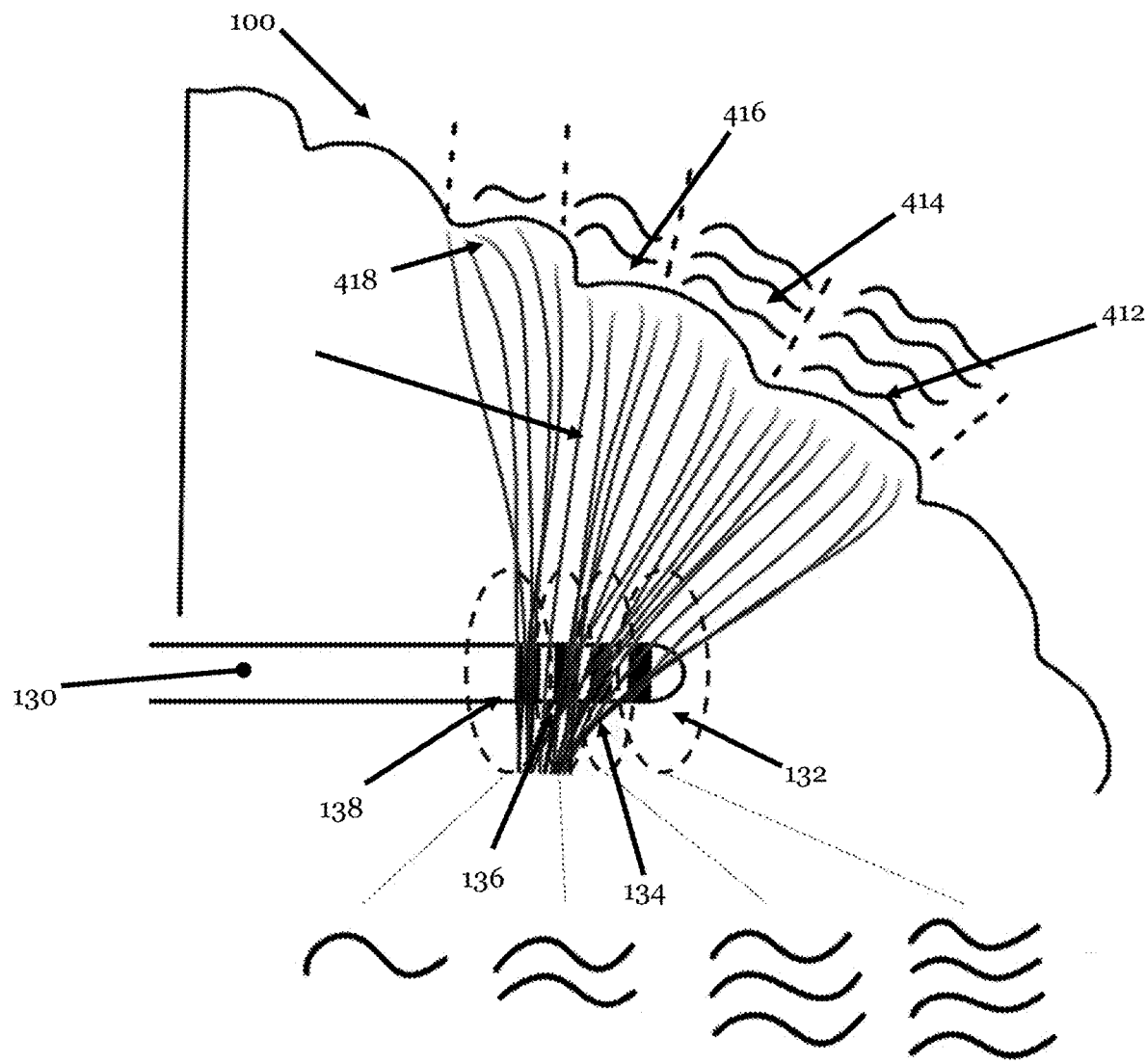
Figure 4B:
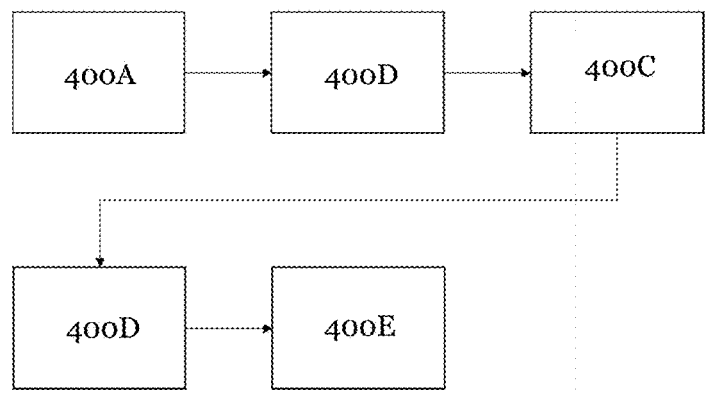
Figure 5:
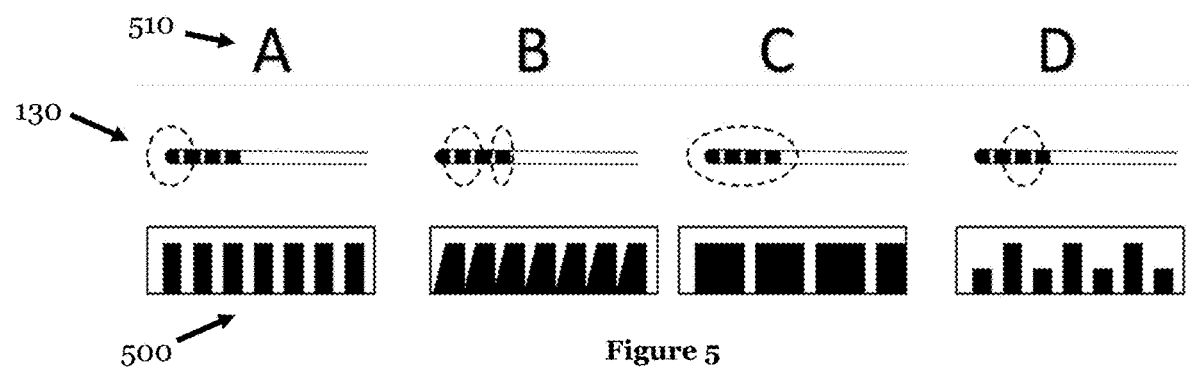
Figure 6:
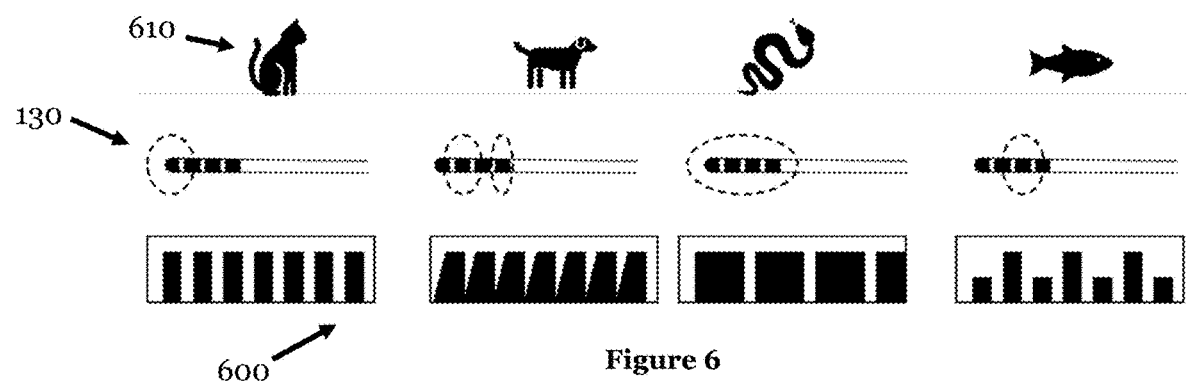
Figure 7:
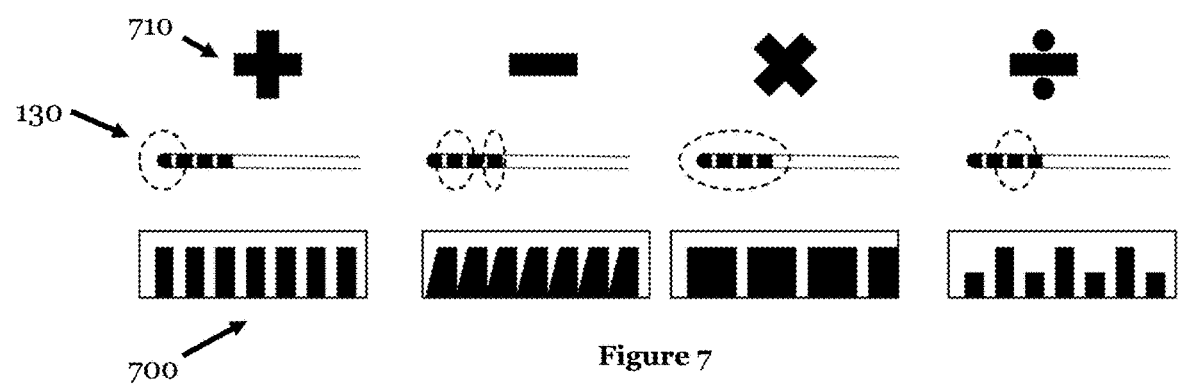
Figure 8:
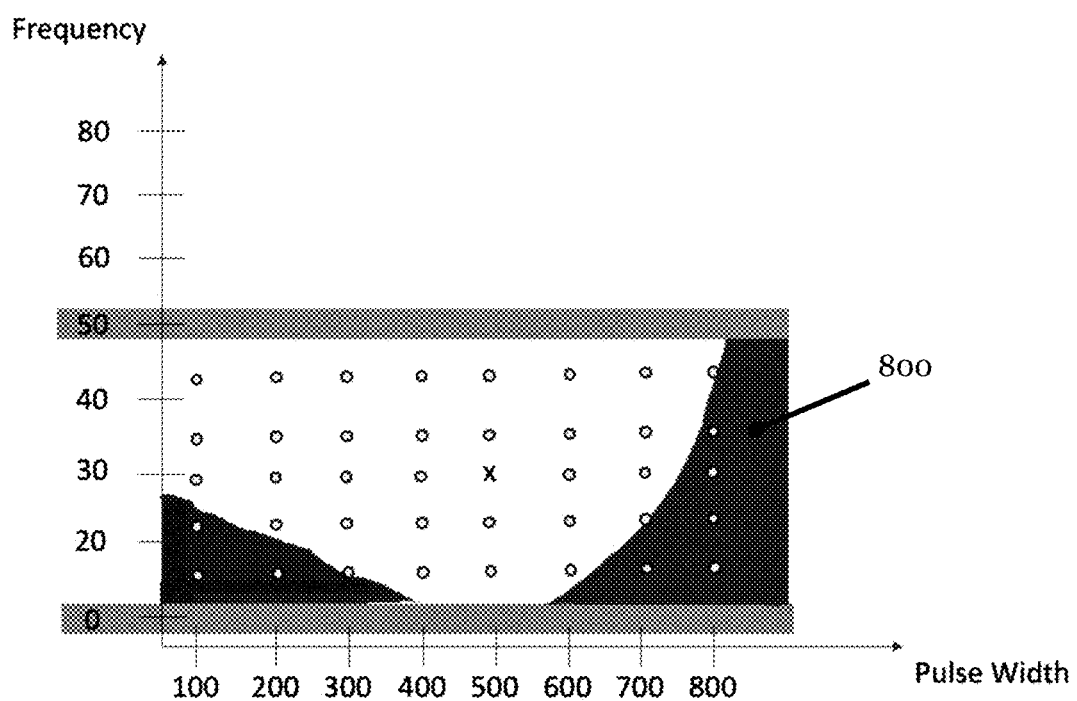
Figure 9:
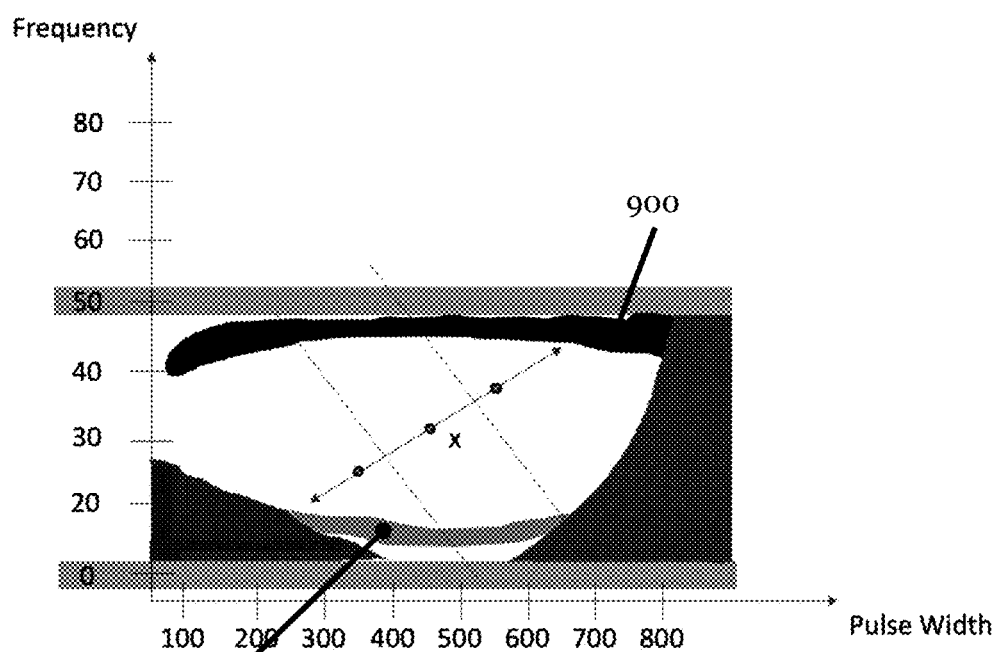
Figure 10:
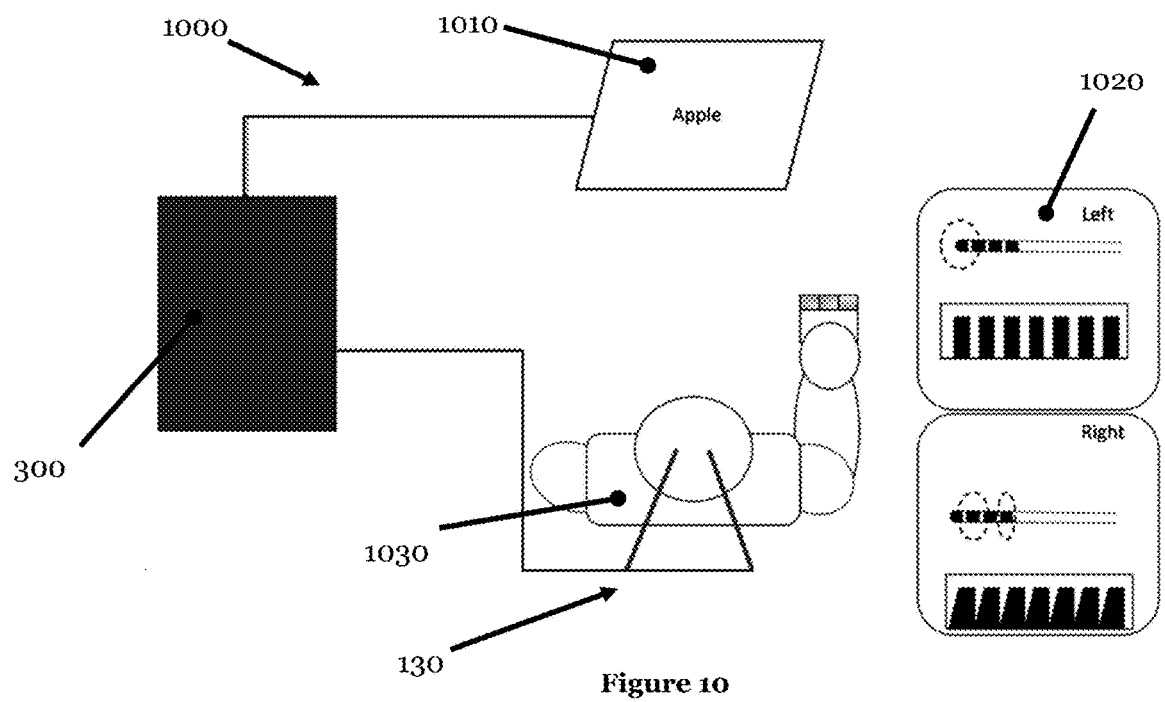
Figure 11:
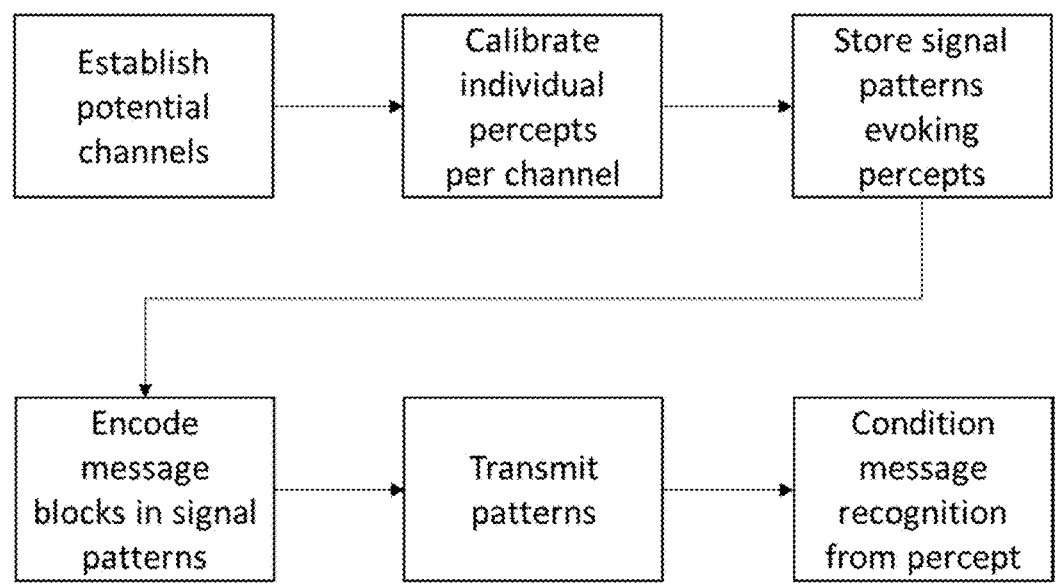
Figure 12:
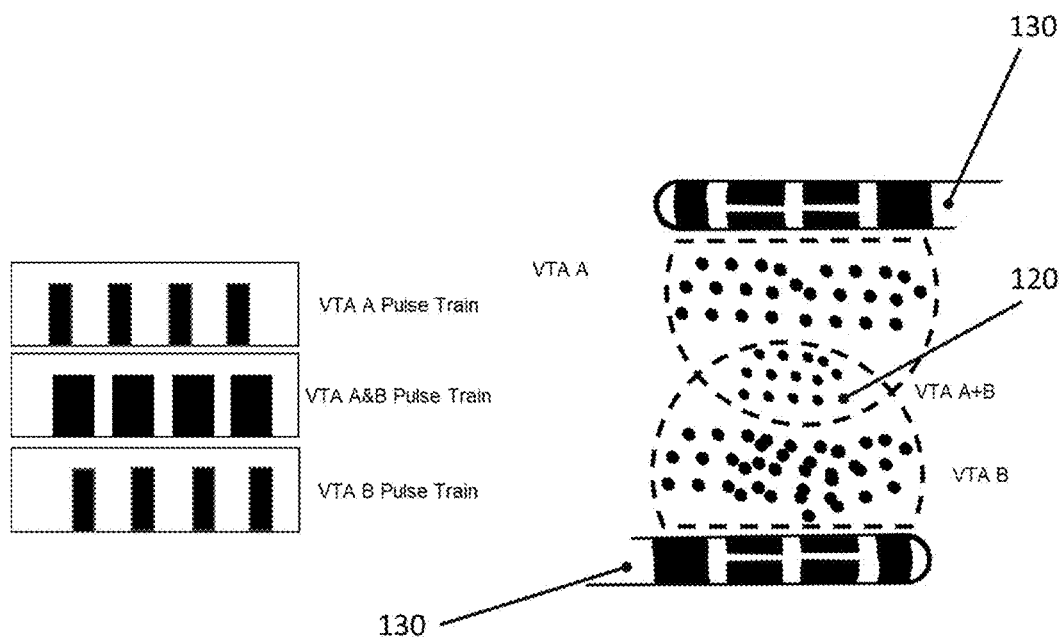

Aspects of the present invention are described in more detail in the following by reference to the accompanying figures. These figures show:

FIG. 1 a diagram illustrating a neuronal stimulation electrode for stimulating afferent axons targeting the sensory cortex of an individual. The neuronal stimulation electrode can be interfaced with a neuronal stimulation system according to an embodiment of the present invention;

FIG. 2 a block diagram of a neuronal stimulation signal generator for driving a neuronal stimulation electrode which can be interfaced with a neuronal stimulation system according to an embodiment of the present invention neuronal stimulation signals;

FIG. 3 a block diagram of a neuronal stimulation system according to an embodiment of the present invention;

FIG. 4a a diagram illustrating the operation of a neuronal communication system according to an embodiment of the present invention;

FIG. 4b a workflow diagram for a procedure for establishing a neuronal communication interface with a human individual;

FIG. 5 a diagram illustrating the encoding of conceptual information using a neuronal communication system according to an embodiment of the present invention;

FIG. 6 a diagram illustrating the encoding of conceptual information using a neuronal communication system according to an embodiment of the present invention;

FIG. 7 a diagram illustrating the encoding of conceptual information using a neuronal communication system according to an embodiment of the present invention;

FIG. 8 a diagram illustrating a parameter space for a neuronal stimulation signal provided by a neuronal stimulation system according to an embodiment of the present invention;

FIG. 9 a diagram illustrating a choice of signal parameters for a neuronal stimulation signal provided by a neuronal stimulation system according to an embodiment of the present invention;

FIG. 10 a diagram illustrating a conceptual learning procedure for learning relations between sensory percepts and conceptual information to be communicated by a neuronal stimulation system according to an embodiment of the present invention;

FIG. 11 a block diagram of a calibration and learning procedure for establishing relations between neuronal stimulation signal and corresponding conceptual information to be communicated by a neuronal stimulation system according to an embodiment of the present invention;

FIG. 12 a diagram illustrating the operation of a neuronal stimulation system according to an embodiment if the present invention that can be interfaced with at two neuronal stimulation electrodes targeting afferent axons of the human brain.

Figure 13:
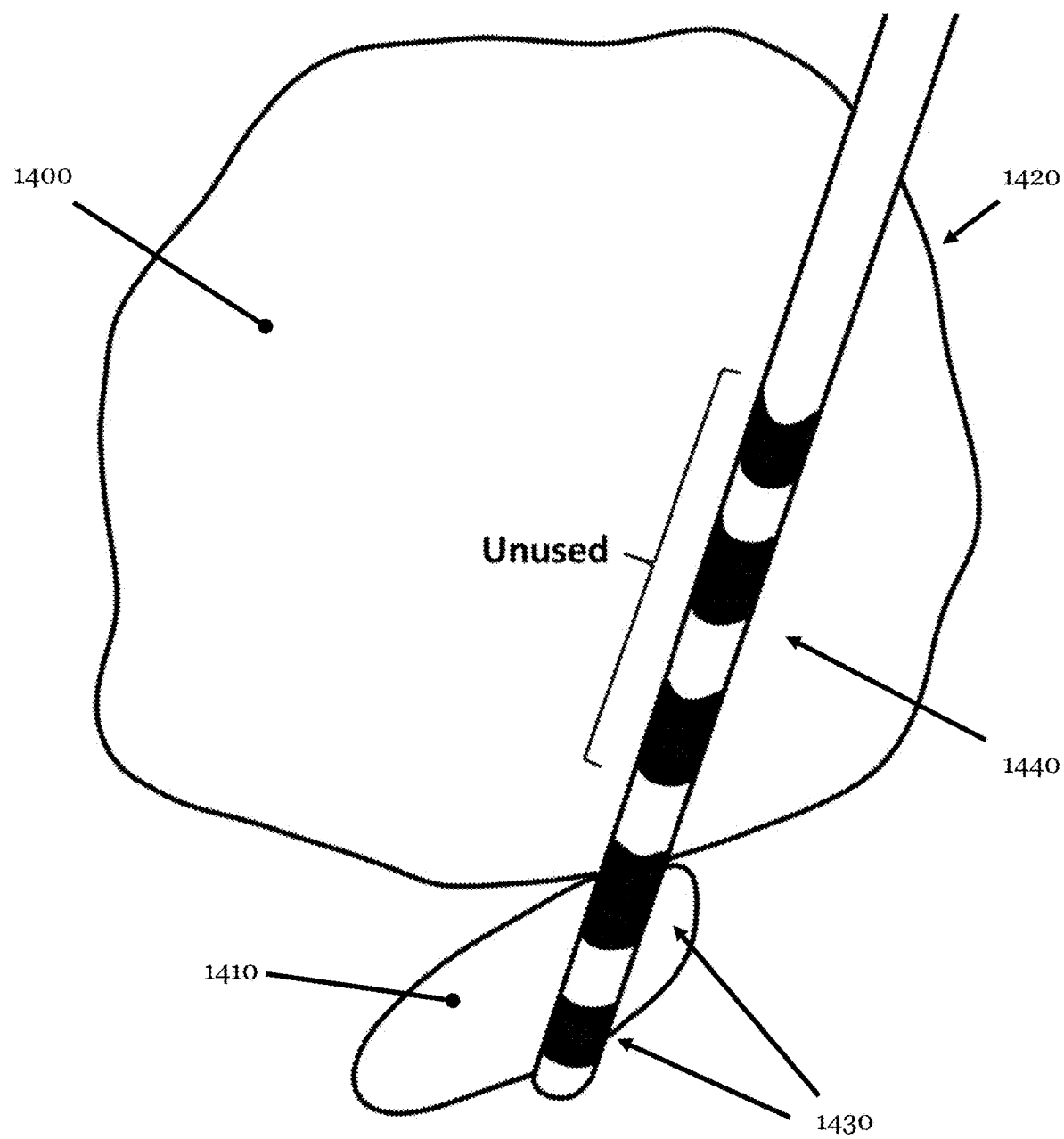

FIG. 13 a magnetic resonance image of a therapeutic multi-contact neuromodulation electrode adapted for modulation of efferent motor axons. Unused contacts of the electrode can also be used for stimulating afferent axons targeting the sensory cortex of an individual via a neuronal stimulation system according to an embodiment of the present invention.

6. DETAILED DESCRIPTION OF SOME EXEMPLARY EMBODIMENTS

In the following, exemplary embodiments of the present invention are described in more detail, with reference to neuronal stimulation and/or communication systems that can be interfaced with neuronal stimulation electrodes such as deep brain stimulation (DBS) electrodes. However, the systems provided by the present invention can also be used with different neuronal stimulation means (e.g. opto-neuronal) that are capable to stimulate afferent axons targeting the sensory cortex of an individual. While specific feature combinations are described in the following with respect to the exemplary embodiments of the present invention, it is to be understood that the disclosure is not limited to such embodiments. In other words, not all features have to be present for realizing the invention, and the embodiments may be modified by combining certain features of one embodiment with one or more features of another embodiment. Specifically, the skilled person will understand that features, components and/or functional elements of one embodiment can be combined with technically compatible features, components and/or functional elements of any other embodiment of the present invention.

FIG. 1 depicts a diagram illustrating a neuronal stimulation electrode 130 for stimulating afferent axons 120 targeting sensory neurons in the cortex 100 of a human brain. The afferent axons 120 target different areas 110, 112 of the cortex 100 that may be related to different sensory modalities (e.g. touch, temperature sense, vision, hearing, etc.) and/or different body regions (e.g. cochlea, retina, hand, tongue, foot etc.) from which the respective sensory modality is perceived by the respective area of the cortex. For instance, the cortical area 110 may be a somatosensory area of the tongue and the cortical area 112 may be a somatosensory area of the left hand.

The afferent axons 120 are connected via synapses (not shown) with their respective target neurons in the respective sensory area 110, 112 of the cortex 100. For instance, the axons 120 may be thalamocortical axons relaying sensory information from the thalamus to the cerebral cortex 100. The neuronal stimulation electrode 130 comprises a plurality of independently controllable electric contacts 132 that are arranged in the vicinity of a bundle of afferent axons targeting the sensory areas 110 and 112 of the cerebral cortex 100. In the illustrated example, the neuronal stimulation electrode 130 is connected to a neuronal stimulation signal generator 140, which is adapted to apply neuronal stimulation signals to the afferent axons 120 via the independently controllable electric contacts 132 of the neuronal stimulation electrode 130. In addition, the neuronal stimulation electrode 130 may further comprise a wireless interface 142 for interfacing the signal generator 140 with a neuronal stimulation system (not shown, see FIG. 3) which may be adapted to determine the waveform and/or the signal parameters (e.g. pulse width, pulse shape, frequency, amplitude, number of pulses etc.) of the neuronal stimulation signals that are generated and applied by the signal generator 140 to the afferent axons 120 via the stimulation electrode 130.

For instance, the neuronal stimulation system may determine the waveform and/or the signal parameters of the neuronal stimulation signal such that a desired sensory percept is elicited in a desired area of the sensory cortex of the individual. In some embodiments of the present invention, the cortex 100 of the individual which is receiving the neuronal stimulation signal (i.e. via afferent action potentials of the stimulated afferent axons 120) may associate the corresponding sensory percept with conceptual information such as a letter, a word, an object, a direction, etc.

For example, similar to learning how to understand Morse code, the individual may have previously participated in a conceptual learning procedure (e.g. see FIG. 10) establishing an associative link between a given sensory percept elicited by a given stimulation signal and a corresponding piece of conceptual information (e.g. see FIGS. 5-7) that is to be communicated to the individual via the neuronal stimulation electrode 130.

In this approach no nuclei or neuron-rich grey matter are preferably targeted by the neuronal stimulation electrode 130 but preferably the axon-rich white matter of the brain, which contains the information transmitting pathways the brain uses for natural neural communication. In this manner, the present invention provides a white-matter computer-brain-interface (CBI), i.e. a system that generates and provides electrical signals the brain can interpret as meaningful input. Maximal efficiency for such a white-matter CBI would be accomplished through perfectly selective recruitment of single axonal fibers 120.

In other embodiments of the present invention the electrode 130, the signal generator 140 and/or the wireless interface 142 may also be part of an integrated neuronal stimulation and/or communication system, e.g. if said components are customized for neuronal communication purposes, i.e. for direct neuronal communication. For instance, a neuronal communication system may comprise of specialized communication software running on a multi-purpose computation device such as a smartphone and a customized assembly of signal generator 140 and stimulation electrode 130 which communicate with the multi-purpose communication device via the wireless interface 142 using conventional wireless data transmission technology such as Wi-Fi, Bluetooth and/or NFC.

In other embodiments of the present invention the neuronal stimulation electrode 130 may be directly connected via conducting wires to a neuronal stimulation system comprising a data processing system and a signal generator similar to the signal generator 140. In this case the wireless interface 140 is not needed.

FIG. 2 is a block diagram of a neuronal stimulation signal generator 140 which can be used to apply neuronal stimulation signals to afferent axons 120 via a neuronal stimulation electrode such as the stimulation electrode 130 of FIG. 1. The neuronal stimulation signal generator 140 may comprise a wireless interface 142 for communicating with a remote neuronal stimulation system (e.g. see FIG. 3) which may be adapted to determine, to select and to transmit a waveform and/or signal parameter of the neuronal stimulation signal to the signal generator 140 in order to elicit a desired sensory percept as described above with reference to FIG. 1.

For instance, the neuronal stimulation signal generator 140 may receive digital data packets specifying a desired neuronal stimulation signal via the wireless interface 142. Receiver (RX) circuitry 210 may process (e.g. filter, amplify, mix, down-convert to baseband etc.) the received digital data packets and feed the processed digital data packets to a digital signal processor (DSP) 220 with may comprise an integrated digital-to-analog converter (DAC). The DSP then processes the digital data packets to generate one or more neuronal stimulation signals which may then be amplified and applied to a neuronal stimulation electrode such as electrode 130 of FIG. 1 by an output amplifier (AMP) 230. For instance, the output AMP 230 may for instance be configured to drive four (or any other number) independently controllable electric contacts 132 of a stimulation electrode such as electrode 130 of FIG. 1 via four wires 240.

In other embodiments, the DSP 220 may receive the digital data packets specifying the neuronal stimulation signal also via a wire-based interface or directly from a collocated digital data packets processing circuit (e.g. a CPU) which is adapted to determine the waveform and/or signal parameters of a desired neuronal stimulation signal corresponding to a desired sensory percept to be elicited and/or a desired piece of conceptual information to be communicated to the individual via the neuronal stimulation electrode 130.

FIG. 3 depicts a block-type circuit diagram of a neuronal stimulation and/or communication system 300 according to an embodiment of the present invention. The neuronal stimulation and/or communication system 300 may for instance comprise a wireless interface 310 and transmitter (TX) circuitry 350 for communicating (e.g. via Bluetooth technology) with a neuronal signal generator such as the generator circuit 140 described above with reference to FIG. 2. The TX circuitry 350 may be adapted to process (i.e. filter, modulate, mix, amplify, and/or upconvert) digital data packets to be communicated via the wireless interface 310. The neuronal stimulation and/or communication system 300 may further comprise a digital signal processor (DSP) 340 operably connected with the TX circuitry 350 and adapted to provide digital data packets specifying the waveform and/or the signal parameters (e.g. frequency, phase, pulse width, pulse amplitude, pulse shape, channel count, etc.) of a desired neuronal stimulation signal to be applied via a neuronal stimulation electrode such as the electrode 130 of FIG. 1 and/or a neuronal stimulation signal generator such as signal generator 140 of FIG. 1 and FIG. 2.

The neuronal stimulation and/or communication system 300 may further comprise a general data processing circuitry such as a CPU 320 operably connected to the DSP 340 and at least one digital memory device 330 operably connected to the CPU 320. The CPU 320 and the memory 330 may interact to determine a desired neuronal stimulation signal corresponding to a desired sensory percept and/or a corresponding piece of conceptual information associated with a sensory percept.

For instance, the memory 330 may contain a personalized communication library for the individual, the library storing relations 332 between a plurality of conceptual information blocks and a plurality of corresponding neuronal stimulation signals. For instance, the memory 330 may store such a relation 332 for every letter of the alphabet and/or each number between zero and ten. In other embodiments of the present invention, the memory 330 may also store relations between stimulation signals and other types of conceptual information such as objects, colors, directions, etc.

A key concept of the present invention is the calibration of such a stimulation library for each individual through both, neuroimaging and individualized testing of the individual. Neuroimaging may first be used to identify theoretically possible ranges of activation for an individual stimulation electrode while individualized testing determines which points in the parameter space of stimulation signal parameters (for details see FIGS. 8 and 9 below) have the potential to be perceived and decoded by the cortex of the individual. It should be emphasized that conscious individualized testing of an individual is merely one specific example how to generate the individualized relations 332 stored in the memory 330. In other embodiments such relations 332 may also be obtained from unconscious patients, e.g. through the non-invasive observation of corresponding functional MRI (fMRI) responses on the somatosensory cortex or EEG recordings.

Further, once or while the communication library (i.e. the plurality of relations 332 stored in the memory 330) is established or is being established for an individual a specific training procedure (see FIG. 10) can be executed (again not necessarily in a conscious individual). As long as the cortex of the individual responds to classical conditioning pair learning can be executed. In this context, such a pair consists of a given sensory percept corresponding to a given neuronal stimulation signal and a piece of conceptual information to be associated with said given sensory percept and the corresponding neuronal stimulation signal).

Importantly, the type of information to be conveyed via the neuronal stimulation and/or communication system 300 whether it is visual, conceptual, categorical, auditory etc. can be chosen freely. Any information or message which can be broken down into message blocks (i.e. pieces of conceptual information that can be decoded by the cortex of an individual) can be transmitted. This includes continuous signal sources such as signals needed for e.g. an artificial balance, orientation signals or other measurement (e.g. altimeter) signals. Learning paradigms for continuous signals deviate from classical conditioning, since they involve more interactive training scenarios where utilization of the signal is a relevant success factor (e.g. orientation in an artificial virtual environment using the input signal). Continuous signals (e.g. intensity) also deviate from signal configurations for messages containing sequentially delivered message blocks (e.g. letters in a word associated with the sensory percepts the individual is trained to associate with the respective letter). In the case of continuous signals, intensity (i.e. the one-dimensional information to be transmitted) might be coded via either pulse width or frequency variations (or combinations of the two), while not varying the location and target areas in the sensory cortex targeted by the recruited axon fibers.

FIG. 4 illustrates the operation of a neuronal communication system according to an embodiment of the present invention. For reasons of clarity, the operation is described in a simple setup wherein a single neuronal stimulation electrode 130 comprising four independently controllable electric contacts 132-138 is implanted such into the white-matter region of the brain of an individual that four distinct areas 412-418 of the sensory cortex can be stimulated via stimulating a plurality of afferent axons 120 targeting sensory neurons in the respective area 412-418 of the cortex 110 of the individual. For instance, the afferent axons 120 may be thalamocortical axons belonging to the visual, auditory and/or somatic sensory system of the individual. Due to the cortico-topic organization of the afferent axons 120 a one-to-one correspondence between each electric contact 132-138 of the stimulation electrode 130 and a corresponding area 412-418 of the sensory cortex 100 of the individual can be established. For instance, the waveform and/or the signal parameters of the neuronal stimulation signal that is applied to the contact 132 of the electrode 130 may be determined (e.g. by the neuronal stimulation system 300 of FIG. 3) such that action potentials are only or predominantly elicited in the specific sub-population of the afferent axons 120 that are targeting the desired area 412 of the sensory cortex.

For instance, the area 412 (414, 416, 418) may be linked to/responsible for perceiving touch percepts of the right thumb (index finger, middle finger, ring finger) of the individual. In this sense, the neuronal stimulation electrode 130 of FIG. 4a can be used to establish a four-channel CBI. In this context, the term "channel" is to be understood broadly such that it encompasses any a distinct communication channel to the cortex of an individual over which the cortex is capable of receiving input that can be separated from other such channels.

Because cortical organization varies from individual to individual the neuronal communication library (and the neuronal stimulation signals stored therein) described above with respect to FIG. 3 is preferably established and customized separately for each individual. For instance, from localizing the electrode 130 in post-operative imaging, identifying the contacts 132-138 and fusing this information with DTI-based individual tractography, a neuronal stimulation and/or communication system such as system 300 of FIG. 3 can automatically calculate spatially distinct volumes of tissue activated (VTAs) which can then be used to elicit action potentials of the axon fibers 120 recruited by the stimulation electrode 130. In the shown example, the number of selectively stimulate-able axon fiber populations equals the number of channels (i.e. four) which can be used to send information (i.e. sensory percepts and/or associated pieces of conceptual information) to the respective sensory cortex area 412-418 for interpretation.

In some embodiments the stimulation of the afferent axons 120 may happen in intensities which are eventually under the perception threshold of the individual. In other words, the corresponding sensory percepts are subconscious. The higher the number of distinct fiber pathways terminating in corresponding cortical areas which can be uniquely and selectively stimulated via activated axon fibers 120 around the active contacts 132-138 of the stimulation electrode 130, the more distinct binary signals and/or multi-symbol communication channels can be established.

A binary signal or signal channel is a volume of tissue (axon fibers 120) that is activated or not by a given neuronal stimulation signal (e.g. by a train of current pulses applied form the neuronal stimulation and/or communication system 300 via the neuronal signal generator 140 and/or the neuronal stimulation electrode 130.

Those activated axonal fibers 120 may lead to somatotopically and/or retinotopically organized areas of the sensory cortex. The recruited axonal fibers drive one specific part of the body representation on the cortex into activity, that then in turn can be decoded by the brain and associated with the desired sensory percept and/or conceptual information to be communicated. The activation can be binary (on vs. off or on vs. no stimulation at all) or continuous by modulating the signal strength via frequency and/or amplitude within a defined range (see FIGS. 8 and 9 below).

The workflow illustrated in FIG. 4b summarizes some of the steps that may be performed to establish a neuronal communication channel via a neuronal stimulation electrode such as electrode 130. Note that some or all of the steps 400A-400E may be executed and/or facilitated by the neuronal stimulation and/or communication systems provided by the present invention:

1. 400A: Tractographically reconstruct axonal fibers connecting e.g. the thalamus to the cortical area in question from DTI neuroimaging data of the subject. Said cortical area (and the fibers leading there) should have a somatotopic, retinotopic, etc. organization (this approach works for axons targeting the somatosensory cortex, auditory cortex, V1/V2 cortex etc.)
2. 400B: From post-operative CT or MRI imaging of the individual, localize the neuronal stimulation electrode 130 and model the geometric properties and positions of the electric contacts 132-138.
3. 400C: Calculate the maximum current pulse amplitude (e.g. measured in mA) for which a VTA reaches the outer boundary of the fiber envelope around the electrode 130 for every single electric contact 132-138 (e.g. considering which parts of the axons 120 can be stimulated without causing any unwanted side effects)
4. 400D: The resulting VTAs add up to establish the communication envelope of the electrode 130.
5. 400E: Optimal communication is established by stimulating maximally distinct/separate regions of the cortex in question, i.e. areas 412-416 via the axon fibers 120 leading to the respective area.
   The minimal axon fiber count/bundle diameter is the lower boundary that defines how small a VTA can be to still recruit enough axon fibers 120 to enable communication, ideally each bundle terminates in a different partition of the sensory cortex (which parcellates in a somatotopic fashion).

It should be noted that based on surgical success every electrode location may offer a different bandwidth for communication. The possible bandwidth is determined on the basis of two functions, first the function underlying the step 400D (e.g. if no contacts are in the vicinity of the axon fibers 120 no stimulation can be applied, and no communication channel can be established) and secondly, step 400E.

The function for step 400E characterizes electrode position with respect to the possibility to uniquely stimulate distinct axon fiber populations. As such, not only the position of the stimulation electrode 130, but also the type of electrode (ring-based or directional or other) and the range of possible stimulation patterns play a role (only cathodic or also bipolar stimulations, biphasic stimulations, multi-area stimulation, MICC=multiple independent current control etc.). For instance, systems with MICC have a unique signal source connected to each individual electrode contact 132-138, thereby enabling the neuronal stimulation and/or communication system 300 of FIG. 3 to stimulate with fractionalized currents (e.g. put 20% of the charge on contact 1 and 80% on contact two at the same time) but also to perform simultaneous multi-area stimulation (e.g. stimulate with pulse amplitudes of 3 mA at 20 Hz on contact 132 and with 2 mA at 120 Hz at contact 134 of the same electrode 130).

FIGS. 5-7 illustrate how different neuronal stimulation signals 500, 600, 700 and/or VTAs can be linked by the cortex of an individual to a variety of different types of conceptual information 510, 610, 710 such as different letters, different types of animals and/or different types of abstract mathematical operators. VTA shapes are generated by defined cathode/anode and current configurations, pulse shapes can be blocks, ramps or combinations thereof and may have different frequencies, pulse lengths or alternating stimulation intensities. In the training/calibration phase (see FIG. 10 below) the sensory percepts elicited via a given neuronal stimulation signal and the corresponding VTA shape can be associated with virtually any type of conceptual information such as letters (e.g. ABC), directions (e.g. left, right, half-left, half-right) or concepts (e.g. stop, go, danger) etc.

FIG. 8 illustrates a simple two-dimensional parameter space for a neuronal communication channel such as the channel provided by one of the electrode contacts 132-138 of the neuronal stimulation electrode 130 illustrated in FIG. 1 and FIG. 4a. In this example, the signal parameters are the pulse frequency and the pulse width for a sequence of current pulses such as the pulse sequences shown in FIGS. 5-7.

The gray shaded area around 0 Hz indicates that in this region the frequency of the stimulation signal is too low to elicit any sensory percept in the corresponding region of the sensory cortex of the individual. The gray shade area around 50 Hz indicates another region that is not suited for eliciting meaningful sensory percepts.

Each of the small white circles in FIG. 8 indicate a possible combination of frequency and pulse width that may be used to elicit a distinct (i.e. distinguishable) sensory percept within the cortex area, e.g. area 412 in FIG. 4a corresponding to the respective electric contact, e.g. contact 132 in FIG. 4a, that is used to apply the neuronal stimulation signal characterized by said combination of frequency and pulse width.

The dark gray shaded area 800 indicates parameter ranges that are also not suited for neuronal communication because stimulation signals corresponding to these ranges may result in a degraded capability of the individual to clearly distinguish and/or to localize the corresponding conscious sensory percept.

FIG. 9 illustrates how a communication channel with three distinct symbols (e.g. low middle and high or 1, 2, 3) can be implemented by using three different combinations (indicated by the dark small circles) of signal parameters. The parameter regions 900 and 910 have also been determined to be unsuited for neuronal communication e.g. because of the corresponding stimulation signal inducing pain or being below the consciousness threshold. In this context it should be highlighted that already three such neuronal communication channels, each capable of signaling three symbols, are sufficient to communicate $3^3=27$ different pieces of conceptual information. In other words, a single stimulation electrode such as electrode 130 of FIG. 1 and FIG. 4a having three independently controllable electric contacts may be sufficient to directly communicate each letter of the alphabet and a stop symbol to the individual via direct neuronal communication. For this neuronal communication paradigm to work properly, similar to learning Morse code, the individual has to learn the respective associations between the sensory percepts elicited by each of the 27 different neuronal stimulation signals and each letter of the alphabet.

To stay in the above example, a communication signal can be generated by stimulating the respective electrode contact 132, 134, 136, 138 affecting axon fibers 120 leading to the respective cortex area 412, 414, 416, 418 either one-by-one (essentially training the cortex to associate a signal with a body part in a binary fashion—the part is stimulated or not) or in combination with weak, moderate or strong stimulation sent in combination.

Individually, the levels of stimulation of a specific axon fiber bundle 120 and the associated body part which the individual patient can differentiate (e.g. can the individual tell the difference between different intensity levels of a sensory percept) play a fundamental role in in determining the bandwidth of a neuronal communication channel. In the above example with four areas and three distinguishable intensity levels 81 distinct patterns (i.e. permutations) can be generated, perceived and associated with conceptual information to be communicated via the CBI to the individual. Establishing levels that can be differentiated can be executed on consciously perceivable levels and interviewing the individual undergoing the training procedure (open calibration; see FIG. 10) or by employing EEG recordings from the surface of the skull or other means of electrophysiology to record cortical reactions to subcortical white matter stimulation (closed calibration).

The parcellation of the individual cortex is not known a-priori, although scientific methods (e.g. Transcranial Magnetic Stimulation) are known in the art that can be used to generate such individualized maps. In the absence of an individualized map of cortical body representations in e.g. the somatosensory region as distinct as possible axon fiber bundles 120 can be recruited. In this context, "distinct" or "disjunct" means that every stimulation signal shall recruit axons fiber populations which are not recruited by the other stimulation signals.

An inverse solution can then be calculated to determine which (potentially bipolar and/or biphasic) electrode configuration can recruit the axon fibers most distinctively while avoiding all other fibers as much as possible. In such a step the angle of each axonal structure as it passes the stimulating electrode is considered, as well as factors such as myelinization, axonal diameter and other anatomical properties of relevance for the calculation of electrical conductivity models (e.g. impedance as a function of local scarring or water content in the tissue from edema), consequently optimal stimulation conditions (depending on the actual electrode geometry) for each fiber are calculated and fibers with similar cortical termination zones and geometric proximity are clustered into a channel.

In one embodiment a target axon fiber population is activated via a neuronal stimulation signal having a fixed pulse width and a fixed amplitude (e.g. an electric current in the mA range). The intensity of the elicited sensory percept (e.g. levels 1, 2, 3 in the above example) can then be instantiated via modulations in the frequency of the stimulation signal.

In greater detail: A brute force approach would generate VTAs within the communication envelope of the electrode from pseudo-random stimulation parameters (or alternatively perform a full walk through the multidimensional parameter space) and determine the recruited axon fibers and their likely cortical termination zone. After exhausting the parameter space those stimulation settings (e.g. set of signal parameters) which recruit maximally geometrically distant and non-overlapping cortical zones are stored as neuronal communication channels. This last step can even be achieved as simply as clustering the activated cortical voxel 3D centroid coordinates, each cluster would represent the cortical fiber termination zone addressed by a given channel. Naturally non-VTA based methods which actually approximate singular axon fiber activation from neuronal compartment modeling (e.g. performed via the NEURON software) are even better suited. In this case, streamlined axon fibers from tractography (e.g. DTI tractography) can be used as a stand-in for actual axonal fibers and the termination zones are determined as described above.

FIG. 10 illustrates how such conceptual/perceptional learning procedure 1000 can be implemented to establish a working neuronal communication system/CBI. In the illustrated example, an individual 1030 was implanted with two neuronal stimulation electrodes 130. The individual 1030 receives a given neuronal stimulation signal 1020 generated by the neuronal communication system 300 connected to the stimulation electrodes 130 via conductor wires. In order to associatively link a certain piece of conceptual information (e.g. a letter, an object, etc.) to the applied neuronal stimulation signal 1020 the individual 1030 is presented with the respective piece of conceptual information via a display screen 1010 and/or a speaker (not shown).

Through means of operant and classical conditioning the associations between a given sensory percept and a piece of conceptual information can be imprinted through training and finally be tested in a validation task (e.g. stimulate a sensory percept and ask the individual to identify the corresponding piece of conceptual information without displaying the corresponding visual and/or auditory cue that was used for establishing the associative link during training.

Via such a classical conditioning paradigm visual cues such as words are depicted on the screen 1010 (preceded and followed by visual Start & Stop cues). During word depiction (message) a characteristic neuronal stimulation signal 1020 is applied via the electrodes 130. After a sufficiently long training run with a large number of repetitions the individual can be tested in a validation run. During validation only, the neuronal stimulation signal 1020 is applied (preceded and followed by visual Start & Stop cues, but without the visual depiction of the word in question) and the individual 1030 is asked to complete a forced choice test to identify the word in question. Above-chance accuracy of the forced choice test can be used to rate success.

In a further training run the stimulation intensities may be reduced such, that no conscious percepts are elicited any longer. Sub-conscious perception of the sensory percepts elicited by the neuronal stimulation signals can still encode the messages communicated to the individual 1030.

FIG. 11 shows a block diagram of a calibration and learning procedure for establishing relations between neuronal stimulation signal and corresponding conceptual information to be communicated by a neuronal stimulation system according to an embodiment of the present invention. The personalized communication library is formed through establishing a number of channels (block 1) and the granularity of transmittable sensory percepts (e.g. through calibration, block 2), storing message blocks and associated signal pattern pairs (block 3) and annotating successful interface components (final block) for example by recording post pair-learning phase successful transfer and/or recognition rate performance (decoding of signal patterns by an individual into perceived messages). This can be repeated by encoding a range of messages into the signal patterns (block 4) and transmitting them to the subject (block 5), similar to increasing verbal fluency in a foreign language of a learner by exposing them to a range of books rather than re-reading the same book over and over.

FIG. 12 illustrates another embodiment of the present invention, wherein a neuronal stimulation system can be interfaced with at least two neuronal stimulation electrodes 130 for stimulating afferent axons 120 targeting the sensory cortex of an individual. In this embodiment multiple electrodes are implanted in a way that their time-synchronized stimulation patterns can be used to overlap and more selectively stimulate certain axon fiber targets 120.

FIG. 14 shows a magnetic resonance image of a multi-contact neuromodulation electrode 1420 adapted for neuromodulation of efferent motor axons. The electrode 1420 can also be used for stimulating afferent axons projecting from the thalamus 1400 to the sensory cortex of an individual via a neuronal stimulation system such as the system 300 of FIG. 3. For example, neuronal stimulation signals may be provided by unused contacts 1440 of the neuromodulation electrode 1420 that was implanted for a therapeutic purpose (e.g. neuromodulation of the subthalamic nucleus 1410 via the therapeutic electric contacts 1430).

For instance, in many cases, a DBS electrode that is used as a neuromodulator, e.g. for treatment of Parkinson, is not always active and/or may comprise independently controllable contacts that are not required for achieving the therapeutic purpose. Thus, the neuromodulation electrode can also be used for applying neuronal stimulation signals provided by a system according to the present invention. For DBS electrodes, specifically, some of the electrode contacts 1440 located outside of the stimulation area of interest are completely unused. However, if implantation in e.g. the subthalamic nucleus 1410 is conducted for the tip contacts 1430 to control, for example, the primary Parkinson symptoms more distal contacts could be used in combination with the above disclosed invention to communicate e.g. a continuous gait biofeedback signal into the brain the patient can utilize to navigate better and/or break free from freezing of gait situations. Such a biofeedback signal can consist of e.g. EMG sensor feedback transmitted to the implant via a smartphone, with the EMG glue-on disposable sensors measuring muscle tension or movement patterns or even simple accelerometer data from a smartwatch.

What is claimed is:

1. A system for stimulating sensory neurons in a cortex of an individual, the system comprising:

a processor coupled to a digital signal processor and a non-transitory memory, wherein the non-transitory memory stores relations between a plurality of sensory percepts of the individual and a plurality of respective corresponding neuronal stimulation signals to be applied to at least one afferent axon targeting the sensory neurons in the cortex of the individual, wherein the at least one afferent axon comprises an afferent sensory axon of a central nervous system of the individual, and wherein different sensory percepts of the plurality of sensory percepts are associated with distinct information to be communicated to the individual, and wherein the processor is coupled to transmitter circuitry and is configured to select and transmit at least one neuronal stimulation signal of the plurality of neuronal stimulation signals via the transmitter circuitry to at least one neuronal stimulation device configured to induce a sequence of action potentials in the at least one afferent axon corresponding to the at least one selected neuronal stimulation signal; and wherein the at least one selected neuronal stimulation signal is adapted to induce said sequence of action potentials in the at least one afferent axon and thereby evoke, in the cortex of the individual, at least one respective sensory percept corresponding to the at least one selected neuronal stimulation signal to communicate the distinct information associated with the at least one respective sensory percept to the individual.

2. The system of claim 1, wherein the system further comprises one or more of:
a digital to analog converter;
a radio frequency transmitter;
a radio frequency receiver;
an analog signal amplifier;
a digital signal amplifier;
radio frequency mixing circuitry;
low-pass, high-pass or band-pass circuitry;
wireless communication circuitry; and
impedance matching circuitry.

3. The system of claim 1, wherein the stored relations between the plurality of sensory percepts and the plurality of respective corresponding neuronal stimulation signals are based at least in part on one or more of:
spatial information for the at least one afferent axon;
spatial information for the at least one neuronal stimulation device;
neuronal connectivity information for the at least one afferent axon;
an electric field distribution associated with the at least one neuronal stimulation device;
functional neuroimaging data for the individual;
diffusion tensor imaging data for the individual;
neuroanatomical reference data being relevant for the individual;
cortical excitation data for the individual;
perceptual learning data for the individual;
conceptual learning data for the individual;
sensory perception data for the individual;
behavioral data based at least in part on subjective experiences of the individual; and
an optimization procedure for maximizing the number of sensory percepts that can be simultaneously perceived by the individual when the corresponding neuronal stimulation signal is transmitted to the at least one neuronal stimulation device configured within the cortex of the individual.

4. The system of claim 3, wherein one or more of the perceptual learning data and the conceptual learning data is generated based at least in part on one or more of:
the individual participating in a perceptional or conceptual learning procedure; and
the individual being analyzed by a non-invasive functional neuroimaging device or an invasive electrophysiological recording device while receiving the at least one neuronal stimulation signal.

5. The system of claim 1,
wherein the distinct information comprise conceptual information to be communicated to the individual, and
wherein the at least one neuronal stimulation signal corresponds to the conceptual information to be communicated.

6. The system of claim 5, wherein the non-transitory memory stores relations, specific for the individual, between a plurality of conceptual information and a plurality of corresponding neuronal stimulation signals.

7. The system of claim 6, wherein the stored specific relations are based at least in part on conceptual learning data for the individual, the conceptual learning data associating the plurality of conceptual information with the plurality of corresponding neuronal stimulation signals.

8. The system of claim 5, wherein the conceptual information comprises one or more of: a letter, a number, a color, a direction in space, a word, a sentence, an object, an identity of a person or animal, an instruction for a motor response of the individual, a position, a bio- or neurofeedback signal, a shape, an image or icon, a warning, an association, a degree of similarity, a salience signal, a rhythm, start or stop commands or information, touch information, surface texture information, pressure information, and an electro-magnetic field strength indication.

9. The system of claim 5, wherein the at least one neuronal stimulation device comprises one or more of a neuronal stimulation electrode, an opto-neuronal interface means and a chemical-neuronal interface means.

10. The system of claim 9, wherein the at least one neuronal stimulation device comprises a plurality of independently controllable electric stimulation contacts.

11. The system of claim 9, wherein the at least one neuronal stimulation device comprises at least two independently controllable stimulation electrodes, each comprising a plurality of independently controllable electric contacts.

12. The system of claim 9, wherein the at least one neuronal stimulation device comprises an implantable neuromodulator usable for a therapeutic purpose independent of inducing the sequence of action potentials, wherein at least a portion of the neuromodulator is used to induce the sequence of action potentials.

13. The system of claim 12, wherein the portion of the neuromodulator is a portion that is not used for the therapeutic purpose.

14. The system of claim 5, wherein the at least one afferent axon is a thalamocortical axon.

15. The system of claim 5, wherein the at least one sensory neuron is located in at least one of:
a somatosensory cortex area,
an auditory cortex area
a visual cortex area,
an olfactory cortex area,
a gustatory cortex area,
a somatosensory association cortex area, and
a proprioception cortex area.

16. A method for stimulating sensory neurons in a cortex of an individual, the method comprising:
storing, in a non-transitory memory, relations between a plurality of sensory percepts of the individual and a plurality of respective corresponding neuronal stimulation signals to be applied to at least one afferent axon targeting the sensory neurons in the cortex of the individual, wherein the at least one afferent axon comprises an afferent sensory axon of a central nervous system of the individual, and wherein different sensory percepts of the plurality of sensory percepts are associated with distinct information to be communicated to the individual, and selecting, via a processor, and transmitting, via transmitter circuitry, at least one neuronal stimulation signal of the plurality of neuronal stimulation signals to at least one neuronal stimulation device configured to induce a sequence of action potentials in the at least one afferent axon corresponding to the at least one selected neuronal stimulation signal, wherein the at least one selected neuronal stimulation signal is adapted to induce said sequence of action potentials in the at least one afferent axon and thereby evoke, in the cortex of the individual, at least one respective sensory percept corresponding to the at least one selected neuronal stimulation signal to communicate the distinct information associated with the at least one respective sensory percept to the individual.

17. The method of claim 16, wherein the stored relations between the plurality of sensory percepts and the plurality of respective corresponding neuronal stimulation signals are based at least in part on one or more of:

spatial information for the at least one afferent axon;
spatial information for the at least one neuronal stimulation device;
neuronal connectivity information for the at least one afferent axon;
an electric field distribution associated with the at least one neuronal stimulation device;
functional neuroimaging data for the individual;
diffusion tensor imaging data for the individual;
neuroanatomical reference data being relevant for the individual;
cortical excitation data for the individual;
perceptual learning data for the individual;
conceptual learning data for the individual;
sensory perception data for the individual;
behavioral data based at least in part on subjective experiences of the individual; and
an optimization procedure for maximizing the number of sensory percepts that can be simultaneously perceived by the individual when the corresponding neuronal stimulation signal is transmitted to the at least one neuronal stimulation device configured within the cortex of the individual.

18. The method of claim 17, the method further comprising:

generating one or more of the perceptual learning data and the conceptual learning data based at least in part on one or more of:
the individual participating in a perceptional or conceptual learning procedure; and
the individual being analyzed by a non-invasive functional neuroimaging device or an invasive electrophysiological recording device while receiving the at least one neuronal stimulation signal.

19. A non-transitory memory, wherein the non-transitory memory stores relations between a plurality of sensory percepts of the individual and a plurality of respective corresponding neuronal stimulation signals to be applied to at least one afferent axon targeting the sensory neurons in the cortex of the individual, wherein the at least one afferent axon comprises an afferent sensory axon of a central nervous system of the individual, and wherein different sensory percepts of the plurality of sensory percepts are associated with distinct information to be communicated to the individual, and wherein the non-transitory memory further stores program instructions executable by a processor to:
select and transmit at least one neuronal stimulation signal of the plurality of neuronal stimulation signals via transmitter circuitry to at least one neuronal stimulation device configured to induce a sequence of action potentials in the at least one afferent axon corresponding to the at least one selected neuronal stimulation signal, wherein the at least one selected neuronal stimulation signal is adapted to induce said sequence of action potentials in the at least one afferent axon and thereby evoke, in the cortex of the individual, at least one respective sensory percept corresponding to the at least one selected neuronal stimulation signal to communicate the distinct information associated with the at least one respective sensory percept to the individual.

20. The non-transitory memory of claim 19, wherein the stored relations between the plurality of sensory percepts and the plurality of respective corresponding neuronal stimulation signals are based at least in part on one or more of:

spatial information for the at least one afferent axon;
spatial information for the at least one neuronal stimulation device;
neuronal connectivity information for the at least one afferent axon;
an electric field distribution associated with the at least one neuronal stimulation device;
functional neuroimaging data for the individual;
diffusion tensor imaging data for the individual;
neuroanatomical reference data being relevant for the individual;
cortical excitation data for the individual;
perceptual learning data for the individual;
conceptual learning data for the individual;
sensory perception data for the individual;
behavioral data based at least in part on subjective experiences of the individual; and
an optimization procedure for maximizing the number of sensory percepts that can be simultaneously perceived by the individual when the corresponding neuronal stimulation signal is transmitted to the at least one neuronal stimulation device configured within the cortex of the individual.

* * * * *

UNITED STATES PATENT AND TRADEMARK OFFICE
CERTIFICATE OF CORRECTION

PATENT NO. : 11,344,725 B2
APPLICATION NO. : 16/380036
DATED : May 31, 2022
INVENTOR(S) : Bálint Várkuti It is certified that error appears in the above-identified patent and that said Letters Patent is hereby corrected as shown below:

In the Specification

In Column 13, Line 7, delete "FIG. 4 illustrates" and insert --FIGS. 4a-4b illustrate--.

In Column 18, Line 21, delete "14" and insert --13--.

In the Claims

In Column 20, Line 51, delete "area" and insert --area,--.

Signed and Sealed this
Second Day of August, 2022

Katherine Kelly Vidal
*Director of the United States Patent and Trademark Office*